(12) United States Patent
Saint-Remy (10) Patent No.: US 9,044,507 B2
(45) Date of Patent: Jun. 2, 2015

(54) ELIMINATION OF IMMUNE RESPONSES TO VIRAL VECTORS

(75) Inventor: Jean-Marie Saint-Remy, Grez-Doiceau (BE)

(73) Assignees: LIFE SCIENCES RESEARCH PARTNERS VZW, Leuven (BE); KATHOLIEKE UNIVERSITEIT LEUVEN, Leuven (BE)

( * ) Notice: Subject to any disclaimer, the term of this patent is extended or adjusted under 35 U.S.C. 154(b) by 56 days.

(21) Appl. No.: 12/735,754

(22) PCT Filed: Feb. 16, 2009

(86) PCT No.: PCT/EP2009/051803
§ 371 (c)(1),
(2), (4) Date: Aug. 13, 2010

(87) PCT Pub. No.: WO2009/101204
PCT Pub. Date: Aug. 20, 2009

(65) Prior Publication Data
US 2011/0111502 A1    May 12, 2011

Related U.S. Application Data

(60) Provisional application No. 61/035,826, filed on Mar. 12, 2008.

(30) Foreign Application Priority Data

Feb. 14, 2008  (EP) .................................... 08447008

(51) Int. Cl.
| | | |
|---|---|---|
| *C12N 5/0783* | (2010.01) | |
| *A61K 48/00* | (2006.01) | |
| *A61K 39/12* | (2006.01) | |
| *C07K 14/005* | (2006.01) | |
| *C12N 9/02* | (2006.01) | |
| *C12N 15/86* | (2006.01) | |
| *A61K 39/00* | (2006.01) | |
| *A61K 38/00* | (2006.01) | |

(52) U.S. Cl.
CPC ............. *A61K 48/0083* (2013.01); *A61K 39/00* (2013.01); *A61K 39/12* (2013.01); *A61K 2039/53* (2013.01); *A61K 2039/545* (2013.01); *A61K 2039/57* (2013.01); *C07K 14/005* (2013.01); *C07K 2319/00* (2013.01); *C12N 9/0036* (2013.01); *C12N 15/86* (2013.01); *C12N 2710/10322* (2013.01); *A61K 38/00* (2013.01)

(58) Field of Classification Search
CPC ... A61K 39/12; A61K 39/145; A61K 39/385; C07K 14/075
USPC ...................... 514/21.3, 21.4, 21.5
See application file for complete search history.

(56) References Cited

U.S. PATENT DOCUMENTS

| | | |
|---|---|---|
| 4,886,782 A | 12/1989 | Good et al. |
| 5,863,528 A | 1/1999 | Hawley et al. |
| 6,759,046 B1 | 7/2004 | Gaudernack et al. |
| 7,157,089 B1 | 1/2007 | Mizzen et al. |
| 2003/0049723 A1 | 3/2003 | Zhang et al. |
| 2003/0104570 A1 | 6/2003 | Cabezon Silva et al. |
| 2003/0129205 A1 | 7/2003 | Saint-Remy et al. |
| 2004/0077045 A1 | 4/2004 | Zhang et al. |
| 2005/0196386 A1 | 9/2005 | Blazar et al. |
| 2005/0202044 A1 | 9/2005 | Mizzen et al. |
| 2006/0211091 A1 | 9/2006 | Zhang et al. |
| 2006/0269561 A1 | 11/2006 | Paterson et al. |
| 2007/0160620 A1 | 7/2007 | Mizzen et al. |
| 2010/0330088 A1 | 12/2010 | Saint-Remy |
| 2011/0002903 A1 | 1/2011 | Saint-Remy |
| 2011/0110964 A1 | 5/2011 | Saint-Remy |
| 2012/0009678 A1 | 1/2012 | Saint-Remy |
| 2013/0095133 A1* | 4/2013 | Klatzmann et al. ......... 424/192.1 |

FOREIGN PATENT DOCUMENTS

| | | |
|---|---|---|
| WO | WO 99/58552 | 11/1999 |
| WO | WO 01/70263 | 9/2001 |
| WO | WO 02/00892 | 1/2002 |
| WO | WO 02/095051 | 11/2002 |
| WO | WO 2005/039613 | 5/2005 |
| WO | WO 2007/104715 | 9/2007 |
| WO | WO 2008/017517 | 2/2008 |
| WO | WO 2009/100505 | 8/2009 |
| WO | WO 2009/101204 | 8/2009 |
| WO | WO 2009/101205 | 8/2009 |
| WO | WO 2009/101206 | 8/2009 |
| WO | WO 2009/101207 | 8/2009 |
| WO | WO 2009/101208 | 8/2009 |

OTHER PUBLICATIONS

Zhao et al.; Activated CD4+CD25+ T cells selectively kill B lymphocytes; Blood; vol. 107, No. 10; pp. 3925-3932; May 15, 2006.*
Brinks et al.; Immunogenicity of Therapeutic Proteins: The Use of Animal Models; Pharm Res (2011) 28:2379-2385.*
International Search Report for PCT/EP2009/051803, mailed Aug. 11, 2009.
Aleksza, M. et al., "Altered cytokine expression of peripheral blood lymphocytes in polymyositis and dermatomyositis", Ann. Rheum. Dis., vol. 64, (2005), pp. 1485-1489.
Bolivar, J. et al, "Molecular cloning of a zinc finger autoantigen transiently associated with interphase nucleolus and mitotic centromeres and midbodies. Orthologous proteins with nine CXXC motifs highly conserved form nematodes to humans", J. Biol, Chem., vol. 274, (1999), pp. 36456-36464.

(Continued)

*Primary Examiner* — Jim Ketter
*Assistant Examiner* — Antonio Galisteo Gonzalez
(74) *Attorney, Agent, or Firm* — Nixon & Vanderhye P.C.

(57) ABSTRACT

The present invention relates to the use of immunogenic peptides comprising a T-cell epitope derived from a viral vector antigen and a redox motif such as C-(X)2-[CST] or [CST]-(X)2-C in the prevention and/or suppression of immune responses to viral vectors and in the manufacture of medicaments therefore.

15 Claims, 1 Drawing Sheet

(56) References Cited

OTHER PUBLICATIONS

Braun, M.Y. et al., "Acute rejection in the absence of cognate recognition of allograft by T cells", J. Immunol., vol. 166, No. 8, (2001), pp. 4879-4883.
Brinster, C. et al., "Costimulatory effects of IL-1 on the expansion/differentiation of CD4+CD25+Foxp3+and CD4+CD25+Foxp3—T cells", J. Leukoc. Biol., vol. 84, (2008), pp. 480-487.
Cao, O. et al, Prevention of gene transfer-induced inhibitor formation by nasal administration of human F.IX T cell epitope in a murine model of hemophilia B., Blood, vol. 104, (2004), pp. 121A-122A.
Chen, T. C. et al., Induction of dominant transplantation tolerance by an altered peptide ligand of the male antigen Dby., .J Clin. Invest., vol. 113, No. 12, (2004), pp. 1754-1762.
Davids, B.J. et al., A new family of giardial cysteine-rich non-VSP protein genes and a novel cyst protein, Plos. One., vol. 1, (2006), e44.
De La Cruz, V.F. et al., "The immunologic significance of variation within malaria circumsporozoite protein sequences", J. Immunol., vol. 142, (1989), pp. 3568-3575.
Eberl, G. et al., "Tissue-specific segregation of CD1d-dependent and CD1d-independent NK T cells", J. Immunol., vol. 162, (1999), pp. 6410-6419.
Dobrzynski, E. et al, "Prevention of cytotoxic T lymphocyte responses to factor IX-expressing hepatocytes by gene transfer-induced regulatory T cells", Proc. Natl. Acad Sci. U.S.A., vol. 103, (2006), pp. 4592-4597.
Fomenko, D.E. et al., "Identity and functions of CxxC-derived motifs", Biochemistry, vol. 42, (2003), pp. 11214-11225.
Geluk, A. et al., "HLA-DR binding analysis of peptides from islet antigens in IDDM", Diabetes, vol. 47, (1998), pp. 1594-1601.
Gross, D.A. et al., "Simple conditioning with monospecific CD4+CD25+ regulatory T cells for bone marrow engraftment and tolerance to multiple gene products", Blood, vol. 108, No. 6, (2006), pp. 1841-1848.
Grossman, W.J., et al, "Differential expression of granzymes A and B in human cytotoxic lymphocyte subsets and T regulatory cells", Blood, vol. 104, (2004), pp. 2840-2848.
Hohn, H. et al., "CD4+ tumor-infiltrating lymphocytes in cervical cancer recognize HLA-DR-restricted peptides provided by human papillomavirus-E7", J. Immunol., vol. 163, (1999), pp. 5715-5722.
Hori, S. et al., "Control of regulatory T cell development by the transcription factor Foxp3", Science, vol. 299, (2003), pp. 1057-1061.
Ise, W. et al., "Naïve CD4+ T cells exhibit distinct expression patterns in cytokines and cell surface molecules on their primary responses to varying doses of antigen", J. Immunol., vol. 168, (2002), pp. 3242-3250.
James, E. et al., HY peptides modulate transplantation responses to skin allografts, Int. Immunol., vol. 14, No. 11, (2002), pp. 1333-1342.
Joffre, O. et al., "Induction of antigen-specific tolerance to bone marrow allografts with CD4+CD25+ T lymphocytes", Blood, vol. 103, No. 11, (2004), pp. 4216-4221.
Louis, S. et al., "Contrasting CD25hiCD4+ T cells/FOXP3 patterns in chronic rejection and operational drug-free tolerance", Transplantation, vol. 81, (2006), pp. 398-407.
Maeda, M. et al., "CD1d-independent NKT cells in beta 2-microglobulin-deficient mice have hybrid phenotype and function of NK and T cells", J. Immunol., vol. 172, (2004), pp. 6115-6122.
Maynard, C.L. et al., "Regulatory T cells expressing interleukin 10 develop from Foxp3+ and Foxp3—precursor cells in the absence of interleukin 10", Nat. Immunol., vol. 8, (2007), pp. 931-941.
Qin, W. et al., "Fusion protein of CDR mimetic peptide with Fc inhibit TNF-alpha induced cytotoxicity", Mol. Immunol., vol. 43, (2006), pp. 660-666.
Roopenian, D. et al., "The immunogenomics of minor histocompatibility antigens", Immunol. Rev., vol. 190, (2002), pp. 86-94.
Saez-Borderias, A. et al, "Expression and function of NKG2D in CD4+ T cells specific for human cytomegalovirus", Eur. J. Immunol., vol. 36, (2006), pp. 3198-3206.
Stenstrom, M. et al., "Natural killer T-cell populations in C57BL/6 and NK1.1 congenic BALB.NK mice-a novel thymic subset defined by BALB.NK mice", Immunology, vol. 114, (2005), pp. 336-345.

Sundar, S.K. et al., "Generation of Epstein-Bar virus antigen-specific suppressor T cells in vitro", Int. J. Cancer, vol. 35, (1985), pp. 351-357.
Taylor, A. et al., "T regulatory cells and allergy", Microbes and Infection, vol. 7, (2005), pp. 1049-1055.
Tsuji, N.M. et al, "Antigen-specific, CD4+CD25+ regulatory T cell clones induced in Peyer's patches", Int. Immunol., vol. 15, (2003),pp. 525-534.
Voo, K.S. et al., "Functional characterization of EBV-encoded nuclear antigen 1-specific CD4+ helper and regulatory T cells elicited by in vitro peptide stimulation", Cancer Res., vol. 65, (2005), pp. 1577-1586.
Wang, R.F., "Immune suppression by tumor-specific CD4+ regulatory T-cells in cancer", Semin. Cancer Biol., vol. 16, (2006), pp. 73-79.
Wiker, H.G. et al., "Cloning, expression and significance of MPT53 for identification of secreted proteins of Mycobacterium tuberculosis", Microb. Pathog., vol. 26, (1999), pp. 207-219.
Wood, K.J. et al., "Regulatory T cells in Transplantation tolerance", Nat. Rev. Immunol., vol. 3, (2003), pp. 199-210.
Haveman, L.M. et al., Induction and capture of CD4+ cytotoxic adenoviral specific T-cells in response to pan-DR binding adenoviral epitopes toward immunotherapy, Blood, vol. 106, (2005), Abstract 3238.
International Search Report for PCT/BE2008/000010, mailed Jul. 2, 2008.
Written Opinion of the International Searching Authority for PCT/BE2008/000010, mailed Jul. 2, 2008.
International Search Report for PCT/EP2009/051806, mailed Aug. 11, 2009.
Written Opinion of the International Searching Authority for PCT/EP2009/051806, mailed Aug. 11, 2009.
International Search Report for PCT/EP2009/051804, mailed Aug. 11, 2009.
Written Opinion for PCT/EP2009/051804, mailed Aug. 11, 2009.
International Search Report for PCT/EP2009/051808, mailed Feb. 18, 2010.
EP Examination Report dated Apr. 26, 2013, issued in connection with European Patent Application No. 09 711 066.2.
European Search Report dated Jul. 9, 2013, issued in related European Patent Application No. 13150811.1.
European Search Report dated Jul. 9, 2013, issued in corresponding European Patent Application No. 13151000.0.
Ge et al, "An hsp70 fusion protein vaccine potentiates the immune response against Japanese encephalitis virus", Arch Virol (2007) 152:125-135.
Fan et al, "Co-immunization of BALB/c mice with recombinant immunogens containing G protein fragment and chimeric CTL, epitope of respiratory syncytial virus induces enhanced cellular immunity and high leel of antibody response", Vaccine 23 (2005) pp. 4453-4461.
Carlier et al, "Increased Synapse Formation Obtained by T cell Epitopes Containing a CxxC Motif in Flanking Residues Convert CD4+ T Cells into Cytolytic Effectors", PLOS One, Oct. 2012, vol. 7, Issue 10, e45366, pp. 1-16.
Janssens et al, "CD4+CD25+ T Cells Lyse Antigen-Presenting B Cells by Fas-Fas Ligand Interaction in an Epitope-Specific Manner", The Journal of Immunology 2003; 171:4604-4612.
Savoldo et al, "Geneation of EBV-Specific CD4+ Cytotoxic T Cells from Virus Naïve Individuals", J. Immunol. 2002; 168:909-918.
Official European Examination Report dated Aug. 12, 2014, issued in connection with European Patent Application No. 09 711 066.2.
Official European Examination Report dated Aug. 7, 2014, issued in connection with European Patent Application No. 13 151 000.0.
Heemskerk et al, "Adenovirus-Specific CD4+T Cell Clones Recognizing Endogenous Antigen Inhibit Viral Replication in Vitro through Cognate Interaction", The Journal of Immunology 2006; 177:8851-8859.
Moldovan et al, "CD4 Dimers Constitute the Functional Component Required for T Cell Activation", The Journal of Immunology 2002, 169:6261-6268.
Canadian Examination Report dated Feb. 26, 2015, issued in connection with Canadian Patent Application No. 2,715,484.

\* cited by examiner

US 9,044,507 B2

ELIMINATION OF IMMUNE RESPONSES TO VIRAL VECTORS

This application is the U.S. national phase of International Application No. PCT/EP2009/051803, filed 16 Feb. 2009, which designated the U.S. and claims priority to European Application No. 08447008.7, filed 14 Feb. 2008 and U.S. Application No. 61/035,826, filed 12 Mar. 2008, the entire contents of each of which are hereby incorporated by reference.

FIELD OF THE INVENTION

The present invention relates to immunogenic peptides and their use in preventing and/or suppressing immune responses to viral vectors such as used in gene therapy and in gene vaccination.

BACKGROUND OF THE INVENTION

Viruses offer a great potential as source of vectors for gene therapy and for gene vaccination. Several viruses are currently used for gene therapy, both experimental and in man, including RNA viruses (gamma-retroviruses and lentiviruses) and DNA viruses (adenoviruses, adeno-associated viruses, herpes viruses and poxviruses). The choice of a virus vector is dictated by several factors, such as the time during which transgene expression is required, the target cells that have to be transduced, whether the target cell is dividing or not, the risk related to multi-insertional events and the risk of inducing a vector-orientated immune response. For a recent review see, e.g., Flotte (2007), *J. Cell. Physiol.* 213, 301-305.

Gene therapy is now being considered for the treatment of an increasing number of diseases. These include: (1) autosomal recessive single gene disorders such as cystic fibrosis, haemophilia A and B, chronic granulomatous disease, X-linked severe combined immunodeficiency and familial hyperlipemia; (2) autosomal dominant syndromes; (3) many forms of cancer; (4) infectious diseases; (5) chronic inflammatory syndromes, and; (6) intractable pain. In the future, the therapy of diseases associated with multiple defects or pathogenetic mechanisms, such as diabetes mellitus, may also become feasible.

Gene vaccination has been developed to cope with the poor protection conferred by soluble proteins of a number of pathogens, including viruses such as the human immunodeficiency virus (HIV). It was thought that intracellular delivery of antigens could direct efficient processing into both major histocompatibility complexes (MHC) class I and class II for improved activation of CD8+ and CD4+ T cells, respectively.

The host immune response towards viral vector proteins was soon recognised as a limiting factor in gene therapy. Cells transduced with viral vectors elicit specific T cells, which lead to inflammation and cell lysis, and thereby aborting transgene expression. The results of a recent anti-HIV gene vaccination trial using recombinant adenovirus vectors expressing the HIV gag, pol or Nef gene were reported by Sekaly (2008), *J. Exp. Med.*, 205, 7-12. Surprisingly, it was shown that the presence of a pre-existing immune response towards viral vector proteins had detrimental results on the outcome of vaccination. Thus, in both situations (i.e., either a pre-existing immune response or no pre-existing immune response) the immune response towards vector-related proteins appear to be ominous.

The immune response towards adenovirus provides one of the best examples of this, as vectors derived from adenovirus are used in the setting of both gene therapy and gene vaccination. Adenovirus is highly immunogenic in man and mammals. Upon injection, adenoviruses elicit an acute innate immune response, which results in inflammation and cytotoxicity, which is often transient. This response, however, triggers an adaptive response that leads to the activation of CD4+ and CD8+ T cells. This is observed even with vectors from which most immunogenic proteins have been removed.

The adaptive immune response to adenovirus involves several components: specific antibodies, CD4+ and CD8+ T cells. Viral proteins are processed and presented by host antigen-presenting cells (APC) in the form of peptides bound to (MHC) of class I and II. Thus, such presentation results in activation of specific T cells belonging to the CD8+ or CD4+ subtype, respectively. The function of CD8+ T cells is to lyse cells expressing virus-derived MHC class I peptides. The function of CD4+ T cells is multifaceted: helping B cells to mature and transform into antibody-forming cells, helping CD8+ T cells to acquire full maturation and development of an inflammatory environment. As such, CD4+ specific T cells play a central role in the elaboration of a virus-specific immune response.

Adenoviruses are ubiquitous and more than 50 serotypes have been described. Many subjects are therefore already immunised, which limits the use of vectors derived from such viruses.

Accordingly, in the setting of gene therapy as well as of gene vaccination, it is highly desirable to find ways to prevent and/or suppress immune responses to viral vector proteins.

SUMMARY OF THE INVENTION

The present invention relates in a first aspect to isolated immunogenic peptides for use in preventing or suppressing in a recipient of a viral vector for gene therapy or gene vaccination, the immune responses to said viral vector. More particularly the invention relates to the use of at least one isolated immunogenic peptide for the manufacture of a medicament for preventing or suppressing an immune response to a viral vector, in a recipient of said vector for gene therapy or gene vaccination, the immunogenic peptide comprising (i) a T-cell epitope derived from a protein from said viral vector and (ii) a C-(X)2-[CST] or [CST]-(X)2-C motif.

In a further aspect, the invention relates to the use of at least one isolated immunogenic peptide comprising (i) a T-cell epitope derived from a viral vector protein and (ii) a [CST]-(X)2-[CST] motif, for the manufacture of a medicament for preventing, in a recipient of gene therapy or gene vaccination, activation of CD4+ effector T-cells by a viral vector protein.

In a further aspect, the invention also covers the use of at least one isolated immunogenic peptide comprising (i) a T-cell epitope derived from a viral vector protein and (ii) a [CST]-(X)2-[CST] motif, for the manufacture of a medicament for inducing, in a recipient of gene therapy or gene vaccination, CD4+ regulatory T cells which are cytotoxic to cells presenting a viral vector protein.

In a further aspect, the invention further relates to the use of at least one isolated immunogenic peptide comprising (i) a T-cell epitope derived from a viral vector protein and (ii) [CST]-(X)2-[CST] motif, for the manufacture of a medicament for preventing, in a recipient of gene therapy or gene vaccination, activation of CD8+ effector T-cells by a viral vector protein.

Generally, the invention provides immunogenic peptides comprising (i) a T-cell epitope derived from a viral vector protein and (ii) C-(X)2-[CST] or [CST]-(X)2-C motif for use in preventing or suppressing in a recipient of the viral vector (for gene therapy or gene vaccination) an immune response to the viral vector, preventing activation of CD4+ and/or CD8+ effector T-cells of a recipient by a viral vector protein and inducing in a recipient CD4+ regulatory T cells which are cytotoxic to cells presenting a viral vector protein (or epitope thereof).

In any of the above uses said viral vector protein may be derived from adenovirus, adeno-associated virus, herpes virus or poxvirus or from a viral vector derived from any thereof. Alternatively, said viral vector protein is derived from retrovirus or lentivirus or from a viral vector derived from any thereof.

In any of the above uses, said C-(X)2-[CST] or [CST]-(X)2-C motif in said immunogenic peptide may be adjacent to said T-cell epitope, or be separated from said T-cell epitope by a linker. In particular embodiments, the linker consists of at most 7 amino acids.

In a further embodiment to the immunogenic peptide in the above uses, the C-(X)2-[CST] or [CST]-(X)2-C motif does not naturally occur within a region of 11 amino acids N- or C-terminally adjacent to the T-cell epitope in said viral vector protein. In particular the C-(X)2-[CST] or [CST]-(X)2-C motif is positioned N-terminally of the T-cell epitope. Further in particular embodiments, at least one X in said C-(X)2-[CST] or [CST]-(X)2-C motif is Gly, Ala, Ser or Thr; additionally or alternatively at least on X is His or Pro. In particular embodiments at least one C in the C-(X)2-[CST] or [CST]-(X)2-C motif is methylated.

In particular embodiments of the immunogenic peptide envisaged for the above uses, the immunogenic peptide further comprises an endosomal targeting sequence. Any of the above immunogenic peptides may be produced by chemical synthesis or by recombinant expression.

A further aspect of the invention relates to methods for obtaining a population of viral vector protein-specific regulatory T cells with cytotoxic properties, said methods comprising the steps of:

- providing peripheral blood cells;
- contacting these cells with an immunogenic peptide comprising (i) a T-cell epitope derived from a viral vector protein and (ii) a C-(X)2-[CST] or [CST]-(X)2-C motif; and
- expanding these cells in the presence of IL-2.

A further method of the invention aims at obtaining a population of viral vector protein-specific regulatory T cells with cytotoxic properties, and such methods comprise the steps of:

- providing an immunogenic peptide comprising (i) a T-cell epitope derived from a viral vector protein and (ii) a C-(X)2-[CST] or [CST]-(X)2-C motif;
- administering the immunogenic peptide to a subject; and
- obtaining a population of viral vector protein-specific regulatory T cells from said subject.

Populations of viral vector protein-specific regulatory T cells with cytotoxic properties obtainable by the above methods are also part of the invention, as well as their use for the manufacture of a medicament for preventing or suppressing immune responses to viral vectors in a recipient of gene therapy or gene vaccination.

A further aspect of the invention relates to isolated immunogenic peptides comprising a T-cell epitope from a viral vector protein and, adjacent to the T-cell epitope or separated from the T-cell epitope by a linker, a C-(X)2-[CST] or [CST]-(X)2-C motif.

The invention further encompasses isolated viral vectors characterised in that they comprise at least one viral vector protein comprising a T-cell epitope and adjacent to the T-cell epitope or separated from the T-cell epitope by a linker, a C-(X)2-[CST] or [CST]-(X)2-C motif. More particularly, the invention provides isolated viral vectors characterised in that at least one T-cell epitope present in at least one of the viral vector proteins is modified by insertion in said viral vector protein, adjacent to said T-cell epitope or separated from said T-cell epitope by a linker, of a C-(X)2-[CST] or [CST]-(X)2-C motif.

FIGURE LEGENDS

FIG. 1. Killing of splenic B cells with a T cell line specific for human adenovirus 5 (HAdV-5). For detailed description, see Example 4.

DETAILED DESCRIPTION OF THE INVENTION

Definitions

The term "peptide" when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification.

The term "epitope" when used herein refers to one or several portions (which may define a conformational epitope) of a protein which is/are specifically recognised and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) (eliciting an immune response only when attached to a carrier) and/or comprising one or more T cell epitopes. Typically, said macromolecule is a protein or peptide (with or without polysaccharides) or made of proteic composition and comprises one or more epitopes; said macromolecule can herein alternatively be referred to as "antigenic protein" or "antigenic peptide".

"Gene therapy" can be defined as the insertion, ex vivo or in vivo, of a gene or genes into individual cells or groups of cells (such as tissues or organs), whereby expression of the gene in the cells or groups of cells ensures a therapeutic effect. In many cases gene therapy is carried out to provide a missing gene or allele or to replace a mutant gene or a mutant allele with a functional copy. The "therapeutic gene" is delivered via a carrier called a vector. The most common vector is a viral vector. Upon infection of targeted cells with the viral vector carrying the therapeutic gene, the viral vector unloads its genetic material including the therapeutic gene into the target cells, followed by the generation of the functional protein(s) encoded by the therapeutic gene. Cells targeted by gene therapy can be either somatic cells or germ cells or cell lines. In addition, gene therapy refers to the use of vectors to deliver, either ex vivo or in vivo, a gene that requires overexpression or ectopic expression in a cell or group of cells. The vector can facilitate integration of the new gene in the nucleus or can lead to episomal expression of that gene.

"Gene vaccination" can be defined as the administration of a functional gene (i.e., capable of expressing the protein encoded by the gene) to a subject for the purpose of vaccinating said subject. Thus, gene vaccination (or DNA vaccination) is a variant of the more classical vaccination with peptides, proteins, attenuated or killed germs, etc. Gene vaccination can be performed with naked DNA or, of particular interest in the context of the present invention, with viral vectors.

The term "viral vector protein" when used herein refers to any protein or peptide derived from a viral vector. Typically such proteins are antigenic and comprise one or more epitopes such as T-cell epitopes.

The term "T cell epitope" or "T-cell epitope" in the context of the present invention refers to a dominant, sub-dominant or minor T cell epitope, i.e., a part of an antigenic protein that is specifically recognised and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and able to activate them, among all the possible T cell epitopes of a protein. In particular, a T cell epitope is an epitope bound by MHC class I or MHC class II molecules.

The term "MHC" refers to "major histocompatibility antigen". In humans, the MHC genes are known as HLA ("human leukocyte antigen") genes. Although there is no consistently followed convention, some literature uses HLA to refer to HLA protein molecules, and MHC to refer to the genes encoding the HLA proteins. As such the terms "MHC" and "HLA" are equivalents when used herein. The HLA system in man has its equivalent in the mouse, i.e., the H2 system. The most intensely-studied HLA genes are the nine so-called classical MHC genes: HLA-A, HLA-B, HLA-C, HLA-DPA1, HLA-DPB1, HLA-DQA1, HLA-DQB1, HLA-DRA, and HLA-DRB1. In humans, the MHC is divided into three regions: Class I, II, and III. The A, B, and C genes belong to MHC class I, whereas the six D genes belong to class II. MHC class I molecules are made of a single polymorphic chain containing 3 domains (alpha 1, 2 and 3), which associates with beta 2 microglobulin at cell surface. Class II molecules are made of 2 polymorphic chains, each containing 2 chains (alpha 1 and 2, and beta 1 and 2).

Class I MHC molecules are expressed on virtually all nucleated cells. Peptide fragments presented in the context of class I MHC molecules are recognised by CD8+ T lymphocytes (cytotoxic T lymphocytes or CTLs). CD8+ T lymphocytes frequently mature into cytotoxic effectors which can lyse cells bearing the stimulating antigen. Class II MHC molecules are expressed primarily on activated lymphocytes and antigen-presenting cells. CD4+ T lymphocytes (helper T lymphocytes or HTLs) are activated with recognition of a unique peptide fragment presented by a class II MHC molecule, usually found on an antigen presenting cell like a macrophage or dendritic cell. CD4+ T lymphocytes proliferate and secrete cytokines that either support an antibody-mediated response through the production of IL-4 and IL-10 or support a cell-mediated response through the production of IL-2 and IFN-gamma.

Functional HLAs are characterised by a deep binding groove to which endogenous as well as foreign, potentially antigenic peptides bind. The groove is further characterised by a well-defined shape and physico-chemical properties. HLA class I binding sites are closed, in that the peptide termini are pinned down into the ends of the groove. They are also involved in a network of hydrogen bonds with conserved HLA residues. In view of these restraints, the length of bound peptides is limited to 8-10 residues. However, it has been demonstrated that peptides of up to 12 amino acid residues are also capable of binding HLA class I. Superposition of the structures of different HLA complexes confirmed a general mode of binding wherein peptides adopt a relatively linear, extended conformation.

In contrast to HLA class I binding sites, class II sites are open at both ends. This allows peptides to extend from the actual region of binding, thereby "hanging out" at both ends. Class II HLAs can therefore bind peptide ligands of variable length, ranging from 9 to more than 25 amino acid residues. Similar to HLA class I, the affinity of a class II ligand is determined by a "constant" and a "variable" component. The constant part again results from a network of hydrogen bonds formed between conserved residues in the HLA class II groove and the main-chain of a bound peptide. However, this hydrogen bond pattern is not confined to the N- and C-terminal residues of the peptide but distributed over the whole chain. The latter is important because it restricts the conformation of complexed peptides to a strictly linear mode of binding. This is common for all class II allotypes. The second component determining the binding affinity of a peptide is variable due to certain positions of polymorphism within class II binding sites. Different allotypes form different complementary pockets within the groove, thereby accounting for subtype-dependent selection of peptides, or specificity. Importantly, the constraints on the amino acid residues held within class II pockets are in general "softer" than for class I. There is much more cross reactivity of peptides among different HLA class II allotypes. The sequence of the +/− 9 amino acids of an MHC class II T cell epitope that fit in the groove of the MHC II molecule are usually numbered P1 to P9. Additional amino acids N-terminal of the epitope are numbered P−1, P−2 and so on, amino acids C-terminal of the epitope are numbered P+1, P+2 and so on.

The term "organic compound having a reducing activity" when used herein refers to compounds, more in particular amino acid sequences, capable of reducing disulfide bonds in proteins. An alternatively used term for these amino acid sequences is "redox motif".

The term "therapeutically effective amount" refers to an amount of the peptide of the invention or derivative thereof, which produces the desired therapeutic or preventive effect in a patient. For example, in reference to a disease or disorder, it is the amount which reduces to some extent one or more symptoms of the disease or disorder, and more particularly returns to normal, either partially or completely, the physiological or biochemical parameters associated with or causative of the disease or disorder. According to one particular embodiment of the present invention, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "natural" when used herein referring to a sequence relates to the fact that the sequence is identical to a naturally occurring sequence or is identical to part of such naturally occurring sequence. In contrast therewith the term "artificial" refers to a sequence which as such does not occur in nature. Unless otherwise specified, the terms natural and artificial thus exclusively relate to a particular amino acid (or nucleotide) sequence (e.g. the sequence of the immunogenic peptide, a sequence comprised within the immunogenic peptide en epitope sequence) and do not refer to the nature of the immunogenic peptide as such. Optionally, an artificial sequence is obtained from a natural sequence by limited modifications such as changing one or more amino acids within the naturally occurring sequence or by adding amino acids N- or C-terminally of a naturally occurring sequence. Amino acids are referred to herein with their full name, their three-letter abbreviation or their one letter abbreviation.

Motifs of amino acid sequences are written herein according to the format of Prosite (Hulo et al. (2006) *Nucleic Acids Res.* 34 (Database issue D227-D230). The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen -. Repetition of an identical element within a motif can be indicated by placing behind that element a numerical value or a numerical range between parentheses. For example: X(2) corresponds to X-X, X(2, 4) corresponds to X-X or X-X-X or X-X-X-X, A(3) corresponds to A-A-A.

The term "homologue" when used herein with reference to the epitopes used in the context of the invention, refer to molecules having at least 50%, at least 70%, at least 80%, at least 90%, at least 95% or at least 98% amino acid sequence identity with the naturally occurring epitope sequence, thereby maintaining the ability of the epitope to bind an antibody or cell surface receptor of a B and/or T cell. Particular embodiments of homologues of an epitope correspond to the natural epitope sequence modified in at most three, more particularly in at most two, most particularly in one amino acid.

The term "derivative" when used herein with reference to the peptides of the invention refers to molecules which contain at least the peptide active portion (i.e. capable of eliciting cytolytic CD4+ T cell activity) and, in addition thereto comprises a complementary portion which can have different purposes such as stabilising the peptides or altering the pharmacokinetic or pharmacodynamic properties of the peptide.

The term "sequence identity" of two sequences when used herein relates to the number of positions with identical nucleotides or amino acids divided by the number of nucleotides or amino acids in the shorter of the sequences, when the two sequences are aligned. In particular embodiments, said sequence identity is from 70% to 80%, from 81% to 85%, from 86% to 90%, from 91% to 95%, from 96% to 100%, or 100%.

The terms "peptide-encoding polynucleotide (or nucleic acid)" and "polynucleotide (or nucleic acid) encoding peptide" when used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. According to one embodiment, the nucleic acid encoding the peptides according to the invention or fragment thereof is a sequence encoding the peptide or fragment thereof originating from a mammal or corresponding to a mammalian, most particularly a human peptide fragment.

The present invention provides ways to prevent and/or suppress immune responses to proteins derived from viral vectors as used in gene therapy and gene vaccination. In particular, the invention provides ways to prevent the development of and/or suppress a CD4+ effector T cells (alternatively referred to as bystander T cells) response. Instead CD4+ regulatory T cells are induced which are capable of specifically inducing apoptosis of APCs presenting T cell epitopes processed from viral vector proteins, thereby preventing the formation of specific antibodies, preventing the maturation of CD8+ T cells and reducing the inflammatory consequences of the proliferation of CD4+ T cells. A consequence of the prevention of full maturation of CD8+ T cells includes the prevention of cytolysis of virally-transduced cells through MHC class I presentation of viral vector-derived peptides. The compounds used to achieve the above are immunogenic peptides encompassing the sequence of a T cell epitope derived from the processing of viral vector proteins attached to a redox motif such as C-(X)2-C. The T cell epitope modified in this way alters the activation pattern and function of CD4+ T cells, either de novo from naïve T cells in a prevention setting, or by modifying the properties of memory T cells, both resulting in potent capacity to induce apoptosis of APC. Thereby the antibody and cellular responses towards viral vector proteins are prevented and/or suppressed. More specifically, the elimination of an APC (dendritic cells, B cells or macrophages, in the setting of primary and secondary immune responses, respectively) presenting MHC class II bound peptides processed from viral vector proteins results in tolerance induction to viral vector proteins. Hence, a major obstacle for efficient gene therapy or gene vaccination is cleared by using the above-described compounds.

In a first aspect the invention relates to isolated immunogenic peptides for use in preventing or suppressing, in a recipient of a viral vector e.g. for gene therapy or gene vaccination, the immune responses to said viral vector. More particularly the invention envisages the use of at least one isolated immunogenic peptide comprising (i) a T-cell epitope derived from a viral vector protein and (ii) a C-(X)2-[CST] or [CST]-(X)2-C motif, for the manufacture of a medicament for preventing or suppressing, in a recipient of gene therapy or gene vaccination, the immune responses to said viral vector. Hence, said immunogenic peptide or the medicament comprising it can be used for prior or prophylactic treatment or immunisation of a recipient of gene therapy or gene vaccination in order to suppress, avoid, reduce partially or totally, or eliminate (partially or totally) immune response(s) induced by the subsequently applied gene therapy or gene vaccination. Likewise, immunogenic peptides according to the invention or the medicaments comprising them can be used for therapeutic treatment or immunisation of a recipient of gene therapy or gene vaccination in order to suppress, reduce partially or totally, or eliminate (partially or totally) ongoing immune response(s) to a viral vector induced by said gene therapy or gene vaccination.

In a further aspect, the invention relates to the use of at least one isolated immunogenic peptide comprising (i) a T-cell epitope derived from a viral vector protein and (ii) a C-(X)2-[CST] or [CST]-(X)2-C motif, for the manufacture of a medicament for preventing, in a recipient of gene therapy or gene vaccination, activation of CD4+ effector T-cells by a viral vector protein.

In a further aspect, the invention also covers the use of at least one isolated immunogenic peptide comprising (i) a T-cell epitope derived from a viral vector protein and (ii) a [CST]-(X)2-[CST]C-(X)2-[CST] or [CST]-(X)2-C motif, for the manufacture of a medicament for inducing, in a recipient of gene therapy or gene vaccination, CD4+ regulatory T cells which are cytotoxic to cells presenting a viral vector protein.

In a further aspect, the invention further relates to the use of at least one isolated immunogenic peptide comprising (i) a T-cell epitope derived from a viral vector protein and (ii) C-(X)2-[CST] or [CST]-(X)2-C motif, for the manufacture of a medicament for preventing, in a recipient of gene therapy or gene vaccination, (full) activation or maturation of CD8+ effector T-cells by a viral vector protein.

In the above aspects of the invention, immunogenic peptides according to the invention or the medicaments comprising them can be used for prior or prophylactic treatment or immunisation of a recipient of gene therapy or gene vaccination in order to suppress, avoid, reduce partially or totally, or eliminate (partially or totally) a normally expected activation in the recipient of CD4+ effector T-cells and/or CD8+ T-cells towards the viral vector following or subsequent to the actual gene therapy or gene vaccination. Likewise, immunogenic peptides according to the invention or medicament comprising them can be used for therapeutic treatment or immunisation of a recipient of gene therapy or gene vaccination in order to suppress, reduce partially or totally, or eliminate (partially or totally) activation in the recipient of CD4+ effector T-cells and/or CD8+ T-cells towards the viral vector concurrent with or after the actual gene therapy or gene vaccination. Alternatively, or concurrently with any of the above, immunogenic peptides according to the invention or the medicaments comprising them can be used for prior or prophylactic treatment or immunisation of a recipient of gene therapy or gene vaccination in order to induce a normally unexpected activation in the recipient of viral vector protein-specific CD4+ regulatory T-cells capable of killing cells presenting viral vector antigen(s) following or subsequent to the actual gene therapy or gene vaccination. Likewise, immunogenic peptides according to the invention or the medicaments comprising them can be used for therapeutic treatment or immunisation of a recipient of gene therapy or gene vaccination in order to induce activation in the recipient of viral vector antigen-specific CD4+ regulatory T-cells capable of killing cells presenting viral vector antigen(s). Said induction may happen concurrent with or after the actual gene therapy or gene vaccination.

In any of the uses described hereinabove, the recipient is a mammal, in particular a (non-human) primate or a human.

In any of the above uses said viral vector protein may be a viral protein derived from adenovirus, adeno-associated virus, herpes virus or poxvirus or from a viral vector derived from any thereof. Alternatively, the viral vector protein is derived from retrovirus (such as gamma-retrovirus) or lentivirus or from a viral vector derived from any thereof. In particular embodiments the viral vector protein is a protein present in the viral vector. In particular embodiments the viral protein is a viral protein (encoded by viral DNA).

The cytotoxic regulatory T cells elicited by the immunogenic peptides of the present invention can suppress immune responses to even complex viral vector antigens. A minimum requirement for such cells to be activated is to recognise a cognate peptide presented by MHC class II determinants, leading to apoptosis of the APC, thereby suppressing the responses of T cells (both CD4+ and CD8+ T cells) to all T cell epitopes presented by the APC. An additional mechanism by which cytotoxic regulator T cells can suppress the overall immune response towards complex antigens is by suppressing the activation of bystander T cells.

There are situations in which more than one viral vector antigen contributes to the immune response against the viral vector. Under such circumstances, the same APC may not present all relevant viral vector antigens, as some of such antigens may be taken up by potentially different APCs. It is therefore anticipated that combination of two or more immunogenic peptides may be used for the prevention and suppression of immune responses to a viral vector.

In any of the uses and methods described hereinabove, the immunogenic peptides can be replaced by CD4+ regulatory T-cells primed with the immunogenic peptide, or can be replaced by a nucleotide sequence encoding the immunogenic peptide (e.g. in the form of naked DNA or a viral vector to be administered to an individual instead of the immunogenic peptide). In addition, a combination of multiple immunogenic peptides, i.e. more than 1 (e.g., 2, 3, 4, 5, 6, 7, 8, 9, 10 or more), can be used in any of the above. These aspects of the invention, as well as the further modification of the immunogenic peptide are described in detail hereafter.

The present invention is based upon the finding that an immunogenic peptide, comprising a T cell epitope derived from a viral vector antigen and a peptide sequence having reducing activity is capable of generating a population of CD4+ regulatory T cells, which have a cytotoxic effect on antigen presenting cells. It is additionally based upon the finding that such immunogenic peptide is capable of preventing activation of viral vector antigen-specific CD8+ T cells and/or CD4+ effector T cells.

Accordingly, the invention relates to immunogenic peptides, which comprise at least one T-cell epitope of a viral vector antigen with a potential to trigger an immune reaction, coupled to an organic compound having a reducing activity, such as a thioreductase sequence motif. The T cell epitope and the organic compound are optionally separated by a linker sequence. In further optional embodiments the immunogenic peptide additionally comprises an endosome targeting sequence (e.g. late endosomal targeting sequence) and/or additional "flanking" sequences.

The immunogenic peptides of the invention can be schematically represented as A-L-B or B-L-A, wherein A represents a T-cell epitope of an antigen (of a viral vector protein) with a potential to trigger an immune reaction, L represents a linker and B represents an organic compound having a reducing activity.

The reducing activity of an organic compound can be assayed for its ability to reduce a sulfhydryl group such as in the insulin solubility assay known in the art, wherein the solubility of insulin is altered upon reduction, or with a fluorescence-labelled insulin. The reducing organic compound may be coupled at the amino-terminus side of the T-cell epitope or at the carboxy-terminus of the T-cell epitope.

Generally the organic compound with reducing activity is a peptide sequence. Peptide fragments with reducing activity are encountered in thioreductases which are small disulfide reducing enzymes including glutaredoxins, nucleoredoxins, thioredoxins and other thiol/disulfide oxidoreductases They exert reducing activity for disulfide bonds on proteins (such as enzymes) through redox active cysteines within conserved active domain consensus sequences: C-X(2)-C, C-X(2)-S, C-X(2)-T, S-X(2)-C, T-X(2)-C (Fomenko et al. (2003) *Biochemistry* 42, 11214-11225), in which X stands for any amino acid. Such domains are also found in larger proteins such as protein disulfide isomerase (PDI) and phosphoinositide-specific phospholipase C.

Accordingly, in particular embodiments, immunogenic peptides according to the present invention comprise as redox motif the thioreductase sequence motif [CST]-X(2)-[CST], in a further embodiment thereto, the [CST]-X(2)-[CST] motif is positioned N-terminally of the T-cell epitope. More specifically, in the redox motif at least one of the [CST] positions is occupied by a Cys; thus the motif is either [C]-X(2)-[CST] or [CST]-X(2)-[C]. In the present application such a tetrapeptide will be referred to as "the motif". In particular embodiments peptides of the invention contain the sequence motif [C]-X(2)-[CS] or [CS]-X(2)-[C]. In more particular embodiments peptides contain the sequence motif C-X(2)-S, S-X(2)-C or C-X(2)-C.

As explained in detail further on, the immunogenic peptides of the present invention can be made by chemical synthesis, which allows the incorporation of non-natural amino acids. Accordingly, in the motif of reducing compounds according to particular embodiments of the present invention, C represents either cysteine or another amino acids with a thiol group such as mercaptovaline, homocysteine or other natural or non-natural amino acids with a thiol function. In order to have reducing activity, the cysteines present in the motif should not occur as part of a cystine disulfide bridge. Nevertheless, the motif may comprise modified cysteines such as methylated cysteine, which is converted into cysteine with free thiol groups in vivo.

Either of the amino acids X in the C-(X)2-[CST] or [CST]-(X)2-C motif of particular embodiments of the immunogenic peptides of the invention can be any natural amino acid, including S, C, or T or can be a non-natural amino acid. In particular embodiments X is an amino acid with a small side chain such as Gly, Ala, Ser or Thr. In further particular embodiments, X is not an amino acid with a bulky side chain such as Tyr. In further particular embodiments at least one X in the [CST]-X(2)-[CST] motif is His or Pro.

In the immunogenic peptides of the present invention comprising the (redox) motif described above, the motif is located such that, when the epitope fits into the MHC groove, the motif remains outside of the MHC binding groove. The motif is placed either immediately adjacent to the epitope sequence within the peptide, or is separated from the T cell epitope by a linker. More particularly, the linker comprises an amino acid sequence of 7 amino acids or less. Most particularly, the linker comprises 1, 2, 3, or 4 amino acids. Alternatively, a linker may comprise 6, 8 or 10 amino acids. Typical amino acids used in linkers are serine and threonine. Example of peptides with linkers in accordance with the present invention are CXXC-G-epitope (SEQ ID NO:1), CXXC-GG-epitope (SEQ ID NO:2), CXXC-SSS-epitope (SEQ ID NO:3), CXXC-SGSG-epitope (SEQ ID NO:4) and the like.

In those particular embodiments of the peptides of the invention where the motif sequence is adjacent to the epitope sequence this is indicated as position P−4 to P−1 or P+1 to P+4 compared to the epitope sequence. Apart from a peptide linker other organic compounds can be used as linker to link the parts of the immunogenic peptide to each other.

The immunogenic peptides of the present invention can further comprise additional short amino acid sequences N or C-terminally of the (artificial) sequence comprising the T cell epitope and the reducing compound (motif). Such an amino acid sequence is generally referred to herein as a 'flanking sequence'. A flanking sequence can be positioned N- and/or C-terminally of the redox motif and/or of the T-cell epitope in the immunogenic peptide. When the immunogenic peptide comprises an endosomal targeting sequence, a flanking sequence can be present between the epitope and an endosomal targeting sequence and/or between the reducing compound (e.g. motif) and an endosomal targeting sequence. More particularly a flanking sequence is a sequence of up to 10 amino acids, or of in between 1 and 7 amino acids, such as a sequence of 2 amino acids.

In particular embodiments of the invention, the redox motif in the immunogenic peptide is located N-terminally from the epitope.

In further particular embodiments, where the redox motif present in the immunogenic peptide contains one cysteine, this cysteine is present in the motif in the position most remote from the epitope, thus the motif occurs as C-X(2)-[ST] or C-X(2)-S N-terminally of the epitope or occurs as [ST]-X(2)-C or S-X(2)-C carboxy-terminally of the epitope.

In certain embodiments of the present invention, immunogenic peptides are provided comprising one epitope sequence and a motif sequence. In further particular embodiments, the motif occurs several times (1, 2, 3, 4 or even more times) in the peptide, for example as repeats of the motif which can be spaced from each other by one or more amino acids (e.g. CXXC X CXXC X CXXC; SEQ ID NO:5), as repeats which are adjacent to each other (CXXC CXXC CXXC; SEQ ID NO:6) or as repeats which overlap with each other CXX-CXXCXXC (SEQ ID NO:7) or CXCCXCCXCC (SEQ ID NO:8)). Alternatively, one or more motifs are provided at both the N and the C terminus of the T cell epitope sequence. Other variations envisaged for the immunogenic peptides of the present invention include peptides containing repeats of a T cell epitope sequence or multiple different T-cell epitopes wherein each epitope is preceded and/or followed by the motif (e.g. repeats of "motif-epitope" or repeats of "motif-epitope-motif"). Herein the motifs can all have the same sequence but this is not obligatory. It is noted that repetitive sequences of peptides which comprise an epitope which in itself comprises the motif will also result in a sequence comprising both the 'epitope' and a 'motif'. In such peptides, the motif within one epitope sequence functions as a motif outside a second epitope sequence. In particular embodiments however, the immunogenic peptides of the present invention comprise only one T cell epitope.

As described above the immunogenic peptides according to the invention comprise, in addition to a reducing compound/motif, a T cell epitope derived from a viral vector antigen. A T cell epitope in a protein sequence can be identified by functional assays and/or one or more in silico prediction assays. The amino acids in a T cell epitope sequence are numbered according to their position in the binding groove of the MHC proteins. In particular embodiments, the T-cell epitope present within the peptides of the invention consists of between 8 and 25 amino acids, yet more particularly of between 8 and 16 amino acids, yet most particularly consists of 8, 9, 10, 11, 12, 13, 14, 15 or 16 amino acids. In a more particular embodiment, the T cell epitope consists of a sequence of 9 amino acids. In a further particular embodiment, the T-cell epitope is an epitope, which is presented to T cells by MHC-class II molecules. In particular embodiments of the present invention, the T cell epitope sequence is an epitope sequence which fits into the cleft of an MHC II protein, more particularly a nonapeptide fitting into the MHC II cleft. The T cell epitope of the immunogenic peptides of the invention can correspond either to a natural epitope sequence of a protein or can be a modified version thereof, provided the modified T cell epitope retains its ability to bind within the MHC cleft, similar to the natural T cell epitope sequence. The modified T cell epitope can have the same binding affinity for the MHC protein as the natural epitope, but can also have a lowered affinity. In particular embodiments the binding affinity of the modified peptide is no less than 10-fold less than the original peptide, more particularly no less than 5 times less. It is a finding of the present invention that the peptides of the present invention have a stabilising effect on protein complexes. Accordingly, the stabilising effect of the peptide-MHC complex compensates for the lowered affinity of the modified epitope for the MHC molecule.

In particular embodiments, the immunogenic peptides of the invention further comprise an amino acid sequence (or another organic compound) facilitating uptake of the peptide into (late) endosomes for processing and presentation within MHC class II determinants. The late endosome targeting is mediated by signals present in the cytoplasmic tail of proteins and correspond to well-identified peptide motifs such as the dileucine-based [DE]XXXL[LI] (SEQ ID NO:9) or DXXLL (SEQ ID NO:10)-motif (e.g. DXXXLL; SEQ ID NO:11), the tyrosine-based YXXØ motif or the so-called acidic cluster motif. The symbol Ø represents amino acid residues with a bulky hydrophobic side chains such as Phe, Tyr and Trp. The late endosome targeting sequences allow for processing and efficient presentation of the antigen-derived T cell epitope by MHC-class II molecules. Such endosomal targeting sequences are contained, for example, within the gp75 protein (Vijayasaradhi et al. (1995) *J Cell Biol* 130, 807-820), the human CD3 gamma protein, the HLA-BM β (Copier et al. (1996) *J. Immunol.* 157, 1017-1027), the cytoplasmic tail of the DEC205 receptor (Mahnke et al. (2000) *J Cell Biol* 151, 673-683). Other examples of peptides which function as sorting signals to the endosome are disclosed in the review of Bonifacio and Traub (2003) *Annu. Rev. Biochem.* 72, 395-447. Alternatively, the sequence can be that of a subdominant or minor T cell epitope from a protein, which facilitates uptake in late endosome without overcoming the T cell response towards the viral vector protein-derived T cell epitope.

The immunogenic peptides of the invention can be generated by coupling a reducing compound, more particularly a reducing motif as described herein, N-terminally or C-terminally to a T-cell epitope of the viral vector antigenic protein (either directly adjacent thereto or separated by a linker). Moreover the T cell epitope sequence of the immunogenic peptide and/or the redox motif can be modified and/or one or more flanking sequences and/or a targeting sequence can be introduced (or modified), compared to the naturally occurring T-cell epitope sequence. Accordingly, the resulting sequence of the immunogenic peptide will in most cases differ from the sequence of the viral vector antigenic protein of interest. In this case, the immunogenic peptides of the invention are peptides with an 'artificial', non-naturally occurring sequence.

The immunogenic peptides of the invention can vary substantially in length, e.g. from about 12-13 amino acids (a T-cell epitope of 8-9 amino acids and the 4-amino acid redox motif) to up to 50 or more amino acids. For example, an immunogenic peptide according to the invention may comprise an endosomal targeting sequence of 40 amino acids, a flanking sequence of about 2 amino acids, a motif as described herein of 4 amino acids, a linker of 4 amino acids and a T cell epitope peptide of 9 amino acids. In particular embodiments, the immunogenic peptides of the invention consist of between 12 amino acids and 20 up to 25, 30, 50, 75, 100 or 200 amino acids. In a more particular embodiment, the peptides consist of between 10 and 20 amino acids. More particularly, where the reducing compound is a redox motif as described herein, the length of the immunogenic peptide comprising the epitope and motif optionally connected by a linker is 19 amino acids or less, e.g., 12, 13, 14, 15, 16, 17, 18 or 19 amino acids.

As detailed above, the immunogenic peptides of the invention comprise a reducing motif as described herein linked to a T cell epitope sequence. According to particular embodiments the T-cell epitopes are derived from viral vector proteins which do not comprise within their native natural sequence an amino acid sequence with redox properties within a sequence of 11 amino acids N- or C-terminally adjacent to the T-cell epitope of interest. Most particularly, the invention encompasses generating immunogenic peptides from viral vector antigenic proteins which do not comprise a sequence selected from C-X(2)-S, S-X(2)-C, C-X(2)-C, S-X(2)-S, C-X(2)-T, T-X(2)-C within a sequence of 11 amino acids N- or C-terminally adjacent to the epitope sequence. In further particular embodiments, the present invention provides immunogenic peptides of viral vector antigenic proteins which do not comprise the above-described amino acid sequences with redox properties within their sequence.

In further particular embodiments, the immunogenic peptides of the invention are peptides comprising T cell epitopes, which T cell epitopes do not comprise an amino acid sequence with redox properties within their natural sequence. However, in alternative embodiments, a T cell epitope binding to the MHC cleft may comprise a redox motif such as described herein within its epitope sequence; the immunogenic peptides according to the invention comprising such T-cell epitope must further comprise another redox motif coupled (adjacent of separated by a linker) N- or C-terminally to the epitope such that the attached motif can ensure the reducing activity (contrary to the motif present in the epitope, which is buried within the cleft).

Another aspect of the present invention relates to methods for generating immunogenic peptides of the present invention described herein. Such methods include the identification of T-cell epitopes in a viral vector antigenic protein of interest; ways for in vitro and in silico identification T-cell epitopes are amply known in the art and some aspects are elaborated upon hereafter.

In particular embodiments, methods according to the invention include the generation of immunogenic peptides of the invention including the identified T-cell epitope and a redox motif (with or without linker(s), flanking sequence(s) or endosomal targeting sequence). The generated immunogenic peptides can be assessed for the capability to induce viral vector protein-specific CD4+ regulatory T cells which are cytotoxic for cells presenting (parts of) the viral vector antigenic protein of interest.

Immunogenic peptides according to the invention are generated starting from T cell epitope(s) of the viral vector protein(s) of interest. In particular, the T-cell epitope used may be a dominant T-cell epitope. The identification and selection of a T-cell epitope from viral vector proteins, for use in the context of the present invention is known to a person skilled in the art. For instance, peptide sequences isolated from a viral vector protein are tested by, for example, T cell biology techniques, to determine whether the peptide sequences elicit a T cell response. Those peptide sequences found to elicit a T cell response are defined as having T cell stimulating activity. Human T cell stimulating activity can further be tested by culturing T cells obtained from an individual sensitised to a viral vector antigen with a peptide/epitope derived from the viral vector antigen and determining whether proliferation of T cells occurs in response to the peptide/epitope as measured, e.g., by cellular uptake of tritiated thymidine. Stimulation indices for responses by T cells to peptides/epitopes can be calculated as the maximum CPM in response to a peptide/epitope divided by the control CPM. A T cell stimulation index (S.I.) equal to or greater than two times the background level is considered "positive." Positive results are used to calculate the mean stimulation index for each peptide/epitope for the group of peptides/epitopes tested. Non-natural (or modified) T-cell epitopes can further optionally be tested for their binding affinity to MHC class II molecules. The binding of non-natural (or modified) T-cell epitopes to MHC class II molecules can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al., (2000) *J. Immunology* 164, 3177-3184). The immunogenic peptides of the invention have a mean T cell stimulation index of greater than or equal to 2.0. An immunogenic peptide having a T cell stimulation index of greater than or equal to 2.0 is considered useful as a prophylactic or therapeutic agent. More particularly, immunogenic peptides according to the invention have a mean T cell stimulation index of at least 2.5, at least 3.5, at least 4.0, or even at least 5.0. In addition, such peptides typically have a positivity index (P.I.) of at least about 100, at least 150, at least about 200 or at least about 250. The positivity index for a peptide is determined by multiplying the mean T cell stimulation index by the percent of individuals, in a population of individuals sensitive to a viral vector antigen (e. g., at least 9 individuals, at least 16 individuals or at least 29 or 30, or even more), who have T cells that respond to the peptide (thus corresponding to the SI multiplied by the promiscuous nature of the peptide/epitope). Thus, the positivity index represents both the strength of a T cell response to a peptide (S.I.) and the frequency of a T cell response to a peptide in a population of individuals sensitive to a viral vector antigen. In order to determine optimal T cell epitopes by, for example, fine mapping techniques, a peptide having T cell stimulating activity and thus comprising at least one T cell epitope as determined by T cell biology techniques is modified by addition or deletion of amino acid residues at either the N- or C-terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. T cell epitopes or peptides are selected based on various factors, including the strength of the T cell response to the peptide/epitope (e.g., stimulation index) and the frequency of the T cell response to the peptide in a population of individuals.

Candidate antigens can be screened by one or more in vitro algorithms to identify a T cell epitope sequence within an antigenic protein. Suitable algorithms are described for example in Zhang et al. (2005) *Nucleic Acids Res* 33, W180-W183 (PREDBALB); Salomon & Flower (2006) *BMC Bioinformatics* 7, 501 (MHCBN); Schuler et al. (2007) *Methods Mol Biol.* 409, 75-93 (SYFPEITHI); Dönnes & Kohlbacher (2006) *Nucleic Acids Res.* 34, W194-W197 (SVMHC); Kolaskar & Tongaonkar (1990) *FEBS Lett.* 276, 172-174 and Guan et al. (2003) *Appl Bioinformatics* 2, 63-66 (MHCPred). More particularly, such algorithms allow the prediction within an antigenic protein of one or more nonapeptide sequences which will fit into the groove of an MHC II molecule.

The immunogenic peptides of the invention can be produced by recombinant expression in, e.g., bacterial cells (e.g. *Escherichia coli*), yeast cells (e.g., *Pichia* species, *Hansenula* species, *Saccharomyces* or *Schizosaccharomyces* species), insect cells (e.g. from *Spodoptera frugiperda* or *Trichoplusia ni*), plant cells or mammalian cells (e.g., CHO, COS cells). The construction of the therefore required suitable expression vectors (including further information such as promoter and termination sequences) involves standard recombinant DNA techniques. Recombinantly produced immunogenic peptides of the invention can be derived from a larger precursor protein, e.g., via enzymatic cleavage of enzyme cleavage sites inserted adjacent to the N- and/or C-terminus of the immunogenic peptide, followed by suitable purification.

In view of the limited length of the immunogenic peptides of the invention, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine. Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry which is amply known to the skilled person. In addition, peptides can be linked to each other to form longer peptides using a ligation strategy (chemoselective coupling of two unprotected peptide fragments) as originally described by Kent (Schnolzer & Kent (1992) *Int. J. Pept. Protein Res.* 40, 180-193) and reviewed for example in Tam et al. (2001) *Biopolymers* 60, 194-205. This provides the tremendous potential to achieve protein synthesis which is beyond the scope of SPPS. Many proteins with the size of 100-300 residues have been synthesised successfully by this method. Synthetic peptides have continued to play an ever-increasing crucial role in the research fields of biochemistry, pharmacology, neurobiology, enzymology and molecular biology because of the enormous advances in the SPPS.

The physical and chemical properties of an immunogenic peptide of interest (e.g. solubility, stability) is examined to determine whether the peptide is/would be suitable for use in therapeutic compositions. Typically this is optimised by adjusting the sequence of the peptide. Optionally, the peptide can be modified after synthesis (chemical modifications e.g. adding/deleting functional groups) using techniques known in the art.

Accordingly, in yet a further aspect, the present invention provides methods for generating viral vector antigen-specific cytotoxic T cells (Tregs or CD4+ regulatory T-cells) either in vivo or in vitro (ex vivo). In particular said T cells are cytotoxic towards any cell presenting a viral vector antigen and are obtainable as a cell population. The invention extends to such (populations of) viral vector antigen-specific cytotoxic Tregs obtainable by the herein described methods.

In particular embodiments, methods are provided which comprise the isolation of peripheral blood cells, the stimulation of the cell population in vitro by contacting an immunogenic peptide according to the invention with the isolated peripheral blood cells, and the expansion of the stimulated cell population, more particularly in the presence of IL-2. The methods according to the invention have the advantage that higher numbers of Tregs are produced and that the Tregs can be generated which are specific for the viral vector antigenic protein (by using a peptide comprising an antigen-specific epitope). Alternatively, viral vector protein-specific cytotoxic T cells may be obtained by incubation in the presence of APCs presenting a viral vector protein-specific immunogenic peptide according to the invention after transduction or transfection of the APCs with a genetic construct capable of driving expression of such immunogenic peptide. Such APCs may in fact themselves be administered to a subject in need to trigger in vivo in said subject the induction of the beneficial subset of cytotoxic CD4+ T-cells.

In an alternative embodiment, the Tregs can be generated in vivo, i.e. by the administration of an immunogenic peptide provided herein to a subject, and collection of the Tregs generated in vivo.

The viral vector protein- or antigen-specific regulatory T cells obtainable by the above methods are of particular interest for use in the manufacture of a medicament for preventing or suppressing in a recipient of gene therapy or gene vaccination the immune response to a viral vector, i.e., for any of the above-described uses of the immunogenic peptides of the invention, said peptides can be replaced by said viral vector protein- or antigen-specific Tregs. Both the use of allogeneic and autogeneic cells is envisaged. Any method comprising the administration of said viral vector protein- or antigen-specific Tregs to a subject in need (i.e., for preventing or suppressing immune response(s) to a viral vector) is also known as adoptive cell therapy. Such therapy is of particular interest in case of treating acute viral vector protein-specific immune reactions and relapses of such reactions. Tregs are crucial in immunoregulation and have great therapeutic potential. The efficacy of Treg-based immunotherapy depends on the Ag specificity of the regulatory T cells. Moreover, the use of Ag-specific Treg as opposed to polyclonal expanded Treg reduces the total number of Treg necessary for therapy.

The present invention also relates to nucleic acid sequences encoding the immunogenic peptides of the present invention and methods for their use, e.g., for recombinant expression or in gene therapy. In particular, said nucleic acid sequences are capable of expressing the immunogenic peptides of the invention.

The immunogenic peptides of the invention may indeed be administered to a subject in need by using any suitable gene therapy method. In any use or method of the invention for the treatment and/or suppression of immune response(s) to a viral vector, immunisation with an immunogenic peptide of the invention may be combined with adoptive cell transfer of (a population of) Tregs specific for said immunogenic peptide and/or with gene therapy. When combined, said immunisation, adoptive cell transfer and gene therapy can be used concurrently, or sequentially in any possible combination.

In gene therapy, recombinant nucleic acid molecules encoding the immunogenic peptides can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognised by the cells normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilising endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding an immunogenic peptide according to the invention is provided. In particular embodiments, the vector is generated such that the nucleic acid molecule sequence is expressed only in a specific tissue. Methods of achieving tissue-specific gene expression are well known in the art, e.g., by placing the sequence encoding an immunogenic peptide of the invention under control of a promoter, which directs expression of the peptide specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for an immunogenic peptide according to the invention may be used in gene therapy. In particular embodiments of the present invention wherein the immunogenic peptide is delivered through gene transfer, this can be ensured as part of the gene therapy to which the patient in subjected. Accordingly the immunogenic protein is delivered simultaneously with the viral vector itself (which is expected to generate the immune reaction).

Where the administration of one or more peptides according to the invention is ensured through gene transfer (i.e. the administration of a nucleic acid which ensures expression of peptides according to the invention in vivo upon administration), the appropriate dosage of the nucleic acid can be determined based on the amount of peptide expressed as a result of the introduced nucleic acid.

The medicament of the invention is usually, but not necessarily, a (pharmaceutical) formulation comprising as active ingredient at least one of the immunogenic peptides of the invention, a (population of) Tregs specific for said immunogenic peptide or a gene therapeutic vector capable of expressing said immunogenic peptide. Apart from the active ingredient(s), such formulation will comprise at least one of a (pharmaceutically acceptable) diluent, carrier or adjuvant. Typically, pharmaceutically acceptable compounds (such as diluents, carriers and adjuvants) can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated. In particular, the pharmaceutical compositions of the invention are vaccines for prophylactic or therapeutic application.

The medicament or pharmaceutical composition of the invention may need to be administered to a subject in need as part of a prophylactic or therapeutic regimen comprising multiple administrations of said medicament or composition. Said multiple administrations usual occur sequentially and the time-interval between two administrations can vary and will be adjusted to the nature of the active ingredient and the nature of the condition to be prevented or treated. The amount of active ingredient given to a subject in need in a single administration can also vary and will depend on factors such as the physical status of the subject (e.g. weight, age), the status of the condition to be prevented or treated, and the experience of the treating doctor, physician or nurse.

The term "diluents" refers for instance to physiological saline solutions. The term "adjuvant" usually refers to a pharmacological or immunological agent that modifies (preferably increases) the effect of other agents (e.g., drugs, vaccines) while having few if any direct effects when given by themselves. As one example of an adjuvant aluminium hydroxide (alum) is given, to which an immunogenic peptide of the invention can be adsorbed. Further, many other adjuvants are known in the art and can be used provided they facilitate peptide presentation in MHC-class II presentation and T cell activation. The term "pharmaceutically acceptable carrier" means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Immunogenic peptides, homologues or derivatives thereof according to the invention (and their physiologically acceptable salts or pharmaceutical compositions all included in the term "active ingredients") may be administered by any route appropriate to the condition to be prevented or treated and appropriate for the compounds, here the immunogenic proteins to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the condition to be prevented or treated.

The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

A further aspect of the invention relates to isolated immunogenic peptides comprising a T-cell epitope from a viral vector protein and, adjacent to said T-cell epitope or separated from said T-cell epitope by a linker, a [CST]-(X)2-[CST] motif, more particularly a C-(X)2-[CST] or [CST]-(X)2-C motif. In particular embodiments, the viral vector protein is a viral protein. In further particular embodiments the viral vector protein is a capsid protein.

Viral vectors for the purpose of gene therapy or gene vaccination are highly amenable to modifications by means of recombinant nucleic acid technology. In view of the above, a skilled person will further easily envisage that the modification to the viral vector T-cell epitope as applied in the immunogenic peptides and their uses according to the invention can be introduced immediately in the viral vector itself. As such, vaccination with the immunogenic peptides comprising a viral vector T-cell epitope and a redox motif (and/or the corresponding gene vaccination and/or the corresponding adoptive cell transfer) may become redundant as the same beneficial effects can be obtained with a modified viral vector. Hence, the invention further encompasses modified viral vectors defined as isolated viral vectors characterised in that at least one T-cell epitope present in at least one of the viral vector proteins is modified by insertion in said viral vector protein, adjacent to said T-cell epitope or separated from said T-cell epitope by a linker, of a C-(X)2-[CST] or [CST]-(X) 2-C motif motif. More particularly the T-cell epitope is separated from the motif by a linker of at most 7 amino acids. In particular embodiments, isolated viral vectors are provided comprising at least one viral vector protein comprising a T cell epitope and adjacent thereto or separated from said T-cell epitope by a linker, a C-(X)2-[CST] or [CST]-(X)2-C motif, wherein the motif does not naturally occur within the viral vector protein within a sequence of 11 amino acids N- or C-terminally adjacent to the T-cell epitope.

In particular embodiments thereof, said viral vector is further characterised in that said modified T-cell epitope is capable of being presented by an MHC class II determinant. In another embodiment, said isolated viral vectors are further characterised in that their cell transducing properties are not significantly altered compared to the same viral vector not carrying the T-cell epitope modification.

Figure 1:
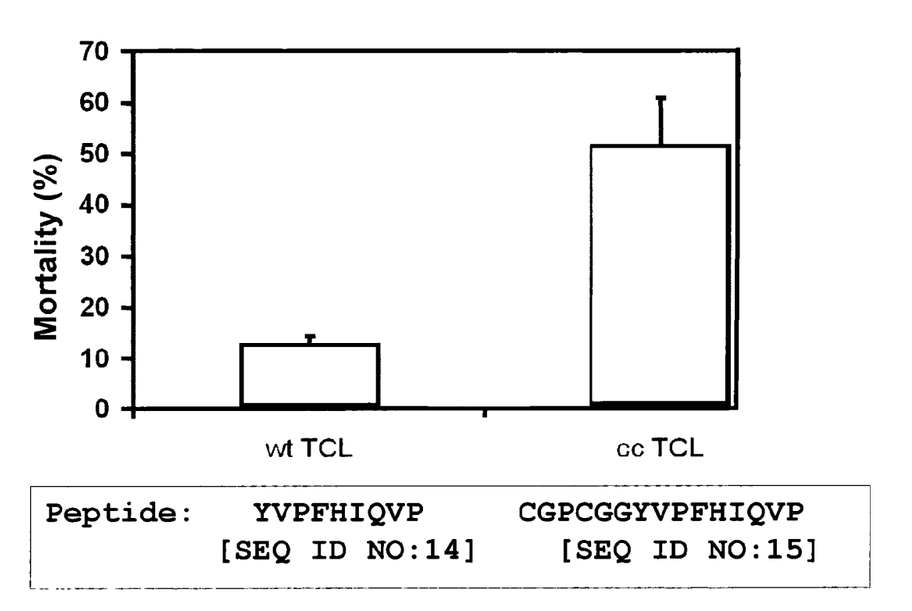

The present invention will now be illustrated by means of the following examples, which are provided without any limiting intention. Furthermore, all references described herein are explicitly included herein by reference.

EXAMPLES

Example 1

In vitro Elicitation of Cytotoxic Regulatory T Cells from Memory T Cells Specific for Viral Vector Protein Adenovirus of serotype 5 (Ad.RR5, E1/E3-deleted) is a commonly used serotype for gene therapy and for gene vaccination. Both in man and mouse a strong immune response is induced towards the major capsid protein hexon. This is used as a model to determine whether cytotoxic regulatory T cells could be derived from cells obtained by immunising mice with the virus vector.

Thus, 5 μL of a solution containing $2\times10^{11}$ viral particles/ml is administered by the intravenous route to 6 weeks old C57Bl/6 mice. Ten days later, the spleen of such mice is recovered and CD4+ T cells purified by magnetic sorting.

A T cell epitope was identified within the sequence of the major capsid protein, by a combination of algorithms. A T cell epitope encompassing amino acid residues 912-921 was selected, with sequence: PTLLYVLFEV (SEQ ID NO:12; natural epitope). A synthetic peptide encoding this natural epitope sequence was obtained. A second peptide additionally containing a thioreductase consensus sequence (or redox motif) was synthesised and has the sequence: CHGCPTLLYVLFEV (SEQ ID NO:13; redox motif underlined; modified epitope).

CD4+ T cells obtained from Ad.RR5-immunized mice are cultured in the presence of spleen adherent cells used as antigen-presenting cells preincubated with either peptide of SEQ ID NO:12 or peptide of SEQ ID NO:13.

After several cycles of restimulation, the CD4+ T cells are cloned by limiting dilution and allowed to rest for 10 days. Clones expanded with the peptide of SEQ ID NO:12 are then compared to clones expanded with the peptide of SEQ ID NO:13 in an assay in which purified B cells from naïve C57Bl/6 mice are used as antigen-presenting cells. Said B cells are loaded with peptides of SEQ ID NO:12 or 13 and cultured in the presence of the cloned CD4+ T cells. After an incubation of 18 h, the induction of apoptosis in B cells is measured by binding of annexin V and Facs analysis.

These experiments demonstrate that is possible to induce CD4+ T cells from memory T cells specific for viral vector protein by using viral vector T cell epitopes modified to comprise a thioreductase consensus sequence (redox motif) wherein the induced CD4+ T cells are capable of eliciting apoptosis of cells presenting either the natural or modified viral vector T cell epitope.

Example 2

Preimmunisation with a Viral Vector T Cell Epitope Containing a Thioreductase Consensus Sequence Prevents Subsequent Development of CD4+ Effector T Cells Towards Viral Vector Proteins Preimmunisation (prior to any contact with viral vector protein) is performed with peptides of SEQ ID NO:13 (see Example 1) in order to prevent the development of a CD4+ effector T cells directed against the adenovirus vector proteins.

To this end, a group C57Bl/6 mice are immunised with 25 μg of peptide of SEQ ID NO:13 in CFA (complete Freund's adjuvant; first immunisation) or IFA (incomplete Freund's adjuvant; second and third immunisation). Injections are made subcutaneously at fortnight intervals. A control group of mice receives immunisation with peptide of SEQ ID NO:12 and a third group is immunised with a sham peptide. All mice then receive an intravenous injection containing $10^9$ adenoviral particles (Ad.RR5, see Example 1). Ten days later, the spleen is recovered and CD4+ T cells purified by sorting on magnetic beads.

The capacity of CD4+ T cells to proliferate in the presence of peptide of SEQ ID NO:12 presented by B cells of naëve animals is measured. The same experiment is repeated with the full adenovirus vector instead of the peptide of SEQ ID NO:12.

This experiment indicates that preimmunisation with a viral vector T cell epitope modified to contain a thioreductase consensus sequence (redox motif) is able to prevent subsequent development of CD4+ effector T cells towards the natural T cell epitope (unmodified, not containing the redox motif) presented as peptide or presented comprised in a full vector protein.

Example 3

Suppression of Pre-Existing CD4+ Effector Cells to Viral Vector Proteins by Immunisation with a T Cell Epitope Modified to Comprise a Thioreductase Consensus Sequence The experiment as described in Example 2 is repeated in a setting in which all mice first received an intravenous injection of Ad.RR5 (see Example 1). Ten days later, groups of mice are immunised as above with the peptide of SEQ ID NO:13 (T cell epitope modified to comprise a redox motif; see Example 1), the peptide of SEQ ID NO:12 (natural T cell epitope, unmodified; see Example 1), or with a sham peptide.

Two weeks after the last immunisation with the peptides, spleens are recovered, CD4+ T cells prepared as above and the capacity of CD4+ T cells to proliferate is measured in the presence of adenoviral proteins presented by B cells.

This experiment indicates that immunisation with a viral vector T cell epitope modified to comprise a thioreductase consensus sequence (redox motif) can suppress a CD4+ effector T cell response already existing due to prior immunisation with viral vector proteins.

Example 4

Killing of Splenic B Cells with a T Cell Line Specific for HAdV-5

TCL lines were obtained from mice immunised with natural sequence 555-563 (SEQ ID NO:14; YVPFHIQVP) from Late Protein 2 derived from human adenovirus 5 (HAdV-5) (wt TCL) or with the same sequence but modified by addition of a thioreductase motif (underlined) separated from the first MHC class II anchoring residue by two Gly residues (SEQ ID NO:15; CGPCGGYVPFHIQVP) (cc TCL). Splenic B cells were stained with a fluorescent membrane marker, loaded with peptide of SEQ ID NO:14 and co-cultured with each of the two T cell lines separately. Cell mortality within the B cell population was analysed after 20 hours on a flow cytometer. Mortality was deducted from size exclusion dot-plots (baseline mortality (22%) was subtracted from test samples). Results are depicted in FIG. 1 and illustrate that an immune response to the adenovirus can be eliminated by using a peptide according to the invention, thus proving the validity of this technology as a means to counter immune responses to viral vectors as used in gene therapy and gene vaccination.

The invention claimed is:

1. A method of suppressing, in a mammalian recipient receiving a viral vector for gene therapy or for gene vaccination which encodes a therapeutic protein, an immune response to a protein encoded by said viral vector, other than the therapeutic protein, comprising the step of administering to said recipient an immunogenic peptide of between 12 and 50 amino acids comprising (i) a T-cell epitope of said protein encoded by said viral vector; and (ii) a C-(X)2-[CST] or [CST]-(X)2-C motif, wherein said C-(X)2-[CST] or [CST]-(X)2-C motif is immediately adjacent to said T-cell epitope, or is separated from said T-cell by a linker of at most 7 amino acids.

2. The method of claim 1, wherein said recipient is administered a medicament comprising said immunogenic peptide suppressing, in the recipient of gene therapy or vaccination, activation of CD4+ effector T-cells by a viral vector protein.

3. The method of claim 1, wherein said recipient is administered a medicament further inducing, in the recipient of gene therapy or gene vaccination, CD4+ regulatory T cells which are cytotoxic to cells presenting a viral vector protein.

4. The method of claim 1, wherein said recipient is administered a medicament comprising said immunogenic peptide suppressing, in the recipient of gene therapy or vaccination, activation of CD8+ effector T-cells by a viral vector protein.

5. The method according to claim 1 wherein said viral vector is derived from an adenovirus vector, adeno-associated virus vector, herpes virus vector or poxvirus vector.

6. The method according to claim 1 wherein said viral vector is derived from a retrovirus.

7. The method according to claim 1 wherein said C-(X)2-[CST] or [CST]-(X)2-C motif does not naturally occur within a region of 11 amino acids N- or C-terminally adjacent to the T-cell epitope in said viral vector protein.

8. The method according to claim 1 wherein said immunogenic peptide further comprises an endosomal targeting sequence.

9. The method according to claim 1 wherein said C-(X)2-[CST] or [CST]-(X)2-C motif is positioned N-terminally of the T-cell epitope.

10. The method according to claim 1 wherein at least one X in said C-(X)2-[CST] or [CST]-(X)2-C motif is Gly, Ala, Ser or Thr.

11. The method according to claim 1 wherein at least one X in said C-(X)2-[CST] or [CST]-(X)2-C motif is His or Pro.

12. The method according to claim 1 wherein at least one C in said C-(X)2-[CST] or [CST]-(X)2-C motif is methylated.

13. The method according to claim 1 wherein said immunogenic peptide is produced by chemical synthesis or by recombinant expression.

14. The method according to claim 6 wherein said retrovirus is a lentivirus.

15. The method of claim 1, wherein the viral vector protein is a capsid protein.

* * * * *

```
                        SEQUENCE LISTING

<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: synthetic peptide, thioreductase motif with
      linker sequence
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (6)..(6)
<223> OTHER INFORMATION: Xaa denotes the N-terminal amino acid of a
      T-cell epitope

<400> SEQUENCE: 1

Cys Xaa Xaa Cys Gly Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide, thioreductase motif with
      linker sequence
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (7)..(7)
<223> OTHER INFORMATION: Xaa denotes the N-terminal amino acid of a
      T-cell epitope

<400> SEQUENCE: 2

Cys Xaa Xaa Cys Gly Gly Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide, thioreductase motif with
      linker sequence
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (8)..(8)
<223> OTHER INFORMATION: Xaa denotes the N-terminal amino acid of a
      T-cell epitope

<400> SEQUENCE: 3

Cys Xaa Xaa Cys Ser Ser Ser Xaa
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: synthetic peptide, thioreductase motif with
      linker sequence
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (9)..(9)
<223> OTHER INFORMATION: Xaa denotes the N-terminal amino acid of a
      T-cell epitope

<400> SEQUENCE: 4

Cys Xaa Xaa Cys Ser Gly Ser Gly Xaa
1               5

<210> SEQ ID NO 5
<211> LENGTH: 14
<212> TYPE: PRT
<213> ORGANISM: Artificial Sequence
<220> FEATURE:
<223> OTHER INFORMATION: synthetic peptide, thioreductase motif repeat
<220> FEATURE:
<221> NAME/KEY: MISC_FEATURE
<222> LOCATION: (1)..(14)
<223> OTHER INFORMATION: Xaa at positions 2, 3, 5, 7, 8, 10, 12, and 13
      denote any amino acid

<400> SEQUENCE: 5

Cys Xaa Xaa Cys Xaa Cys Xaa Xaa Cys Xaa Cys Xaa Xaa Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthetic peptide, thioreductase motif repeat
<220> FEATURE:
<221> NAME/KEY: MISC_FEATURE
<222> LOCATION: (1)..(12)
<223> OTHER INFORMATION: Xaa at positions 2, 3, 6, 7, 10, and 11 denote
      any amino acid

<400> SEQUENCE: 6

Cys Xaa Xaa Cys Cys Xaa Xaa Cys Cys Xaa Xaa Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic peptide, thioreductase motif repeat
<220> FEATURE:
<221> NAME/KEY: MISC_FEATURE
<222> LOCATION: (1)..(10)
<223> OTHER INFORMATION: Xaa at positions 2, 3, 5, 6, 8, and 9 denote
      any amino acid

<400> SEQUENCE: 7

Cys Xaa Xaa Cys Xaa Xaa Cys Xaa Xaa Cys
1               5                   10
```

```
<210> SEQ ID NO 8
<211> LENGTH: 10
<212> TYPE: PRT
<213> ORGANISM: Artificial Sequence
<220> FEATURE:
<223> OTHER INFORMATION: synthetic peptide, thioreductase motif repeat
<220> FEATURE:
<221> NAME/KEY: MISC_FEATURE
<222> LOCATION: (1)..(10)
<223> OTHER INFORMATION: Xaa at positions 2, 5, and 8 denote any amino
      acid

<400> SEQUENCE: 8

Cys Xaa Cys Cys Xaa Cys Cys Xaa Cys Cys
1               5                   10

<210> SEQ ID NO 9
<211> LENGTH: 6
<212> TYPE: PRT
<213> ORGANISM: Artificial Sequence
<220> FEATURE:
<223> OTHER INFORMATION: synthetic peptide, late endosome targeting
      signal
<220> FEATURE:
<221> NAME/KEY: MISC_FEATURE
<222> LOCATION: (1)..(1)
<223> OTHER INFORMATION: Xaa denotes aspartate (D or Asp) or glutamate
      (E or Glu)
<220> FEATURE:
<221> NAME/KEY: MISC_FEATURE
<222> LOCATION: (2)..(4)
<223> OTHER INFORMATION: Xaa at positions 2, 3 and 4 denote any amino
      acid
<220> FEATURE:
<221> NAME/KEY: MISC_FEATURE
<222> LOCATION: (6)..(6)
<223> OTHER INFORMATION: Xaa denotes leucine (L or Leu) or isoleucine (I
      or Ile)

<400> SEQUENCE: 9

Xaa Xaa Xaa Xaa Leu Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic peptide, late endosome targeting
      signal
<220> FEATURE:
<221> NAME/KEY: MISC_FEATURE
<222> LOCATION: (2)..(3)
<223> OTHER INFORMATION: Xaa at positions 2 and 3 denote any amino acid

<400> SEQUENCE: 10

Asp Xaa Xaa Leu Leu
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic peptide, late endosome targeting
      signal
<220> FEATURE:
<221> NAME/KEY: MISC_FEATURE
<222> LOCATION: (2)..(5)
<223> OTHER INFORMATION: Xaa at positions 2, 3 and 4 denote any amino
      acid
```

```
<400> SEQUENCE: 11

Asp Xaa Xaa Xaa Leu Leu
1               5

<210> SEQ ID NO 12
<211> LENGTH: 10
<212> TYPE: PRT
<213> ORGANISM: Artificial Sequence
<220> FEATURE:
<223> OTHER INFORMATION: synthetic peptide, T-cell epitope derived from
      major capsid protein of adenovirus serotype 5

<400> SEQUENCE: 12

Pro Thr Leu Leu Tyr Val Leu Phe Glu Val
1               5                   10

<210> SEQ ID NO 13
<211> LENGTH: 14
<212> TYPE: PRT
<213> ORGANISM: Artificial Sequence
<220> FEATURE:
<223> OTHER INFORMATION: synthetic peptide, modified T-cell epitope,
      T-cell epitope derived from major capsid protein of adenovirus
      serotype 5
<220> FEATURE:
<221> NAME/KEY: MISC_FEATURE
<222> LOCATION: (1)..(4)
<223> OTHER INFORMATION: thioreductase motif

<400> SEQUENCE: 13

Cys His Gly Cys Pro Thr Leu Leu Tyr Val Leu Phe Glu Val
1               5                   10

<210> SEQ ID NO 14
<211> LENGTH: 9
<212> TYPE: PRT
<213> ORGANISM: Artificial Sequence
<220> FEATURE:
<223> OTHER INFORMATION: synthetic peptide, T-cell epitope consisting of
      amino acids 555-563 of Late Protein 2 of human adenovirus 5

<400> SEQUENCE: 14

Tyr Val Pro Phe His Ile Gln Val Pro
1               5

<210> SEQ ID NO 15
<211> LENGTH: 15
<212> TYPE: PRT
<213> ORGANISM: Artificial Sequence
<220> FEATURE:
<223> OTHER INFORMATION: synthetic peptide, modified T-cell epitope,
      T-cell epitope consisting of amino acids 555-563 of Late Protein 2
      of human adenovirus 5
<220> FEATURE:
<221> NAME/KEY: MISC_FEATURE
<222> LOCATION: (1)..(4)
<223> OTHER INFORMATION: thioreductase motif
<220> FEATURE:
<221> NAME/KEY: MISC_FEATURE
<222> LOCATION: (5)..(6)
<223> OTHER INFORMATION: Gly-Gly linker

<400> SEQUENCE: 15

Cys Gly Pro Cys Gly Gly Tyr Val Pro Phe His Ile Gln Val Pro
1               5                   10                  15
```